US010408790B2

(12) United States Patent
Pang et al.

(10) Patent No.: US 10,408,790 B2
(45) Date of Patent: Sep. 10, 2019

(54) BUNDLED FIBER OPTIC CAPILLARY ELECTROPHORESIS DETECTION SYSTEM

(71) Applicant: ADVANCED ANALYTICAL TECHNOLOGIES, INC., Ankeny, IA (US)

(72) Inventors: Ho-ming Pang, Ames, IA (US); Wei Wei, Ames, IA (US)

(73) Assignee: Agilent Technologies, Inc., Santa Clara, CA (US)

(*) Notice: Subject to any disclaimer, the term of this patent is extended or adjusted under 35 U.S.C. 154(b) by 318 days.

(21) Appl. No.: 15/001,632

(22) Filed: Jan. 20, 2016

(65) Prior Publication Data

US 2016/0223493 A1    Aug. 4, 2016

Related U.S. Application Data

(63) Continuation of application No. 12/634,349, filed on Dec. 9, 2009, now Pat. No. 9,518,955, which is a continuation-in-part of application No. 11/299,643, filed on Dec. 12, 2005, now abandoned.

(60) Provisional application No. 61/121,043, filed on Dec. 9, 2008.

(51) Int. Cl.
*G01N 21/64* (2006.01)
*G01N 27/447* (2006.01)

(52) U.S. Cl.
CPC ..... *G01N 27/44791* (2013.01); *G01N 21/645* (2013.01); *G01N 21/6428* (2013.01); *G01N 27/447* (2013.01); *G01N 27/44721* (2013.01); *G01N 27/44726* (2013.01); *G01N 27/44782* (2013.01)

(58) Field of Classification Search
None
See application file for complete search history.

(56) References Cited

U.S. PATENT DOCUMENTS

| 3,916,197 | A |   | 10/1975 | Fulwyler |
|---|---|---|---|---|
| 4,968,632 | A |   | 11/1990 | Brauer et al. |
| 5,021,646 | A | * | 6/1991 | Weinberger ...... G01N 27/44708 204/603 |
| 5,302,272 | A |   | 4/1994 | Klein |
| 5,312,535 | A |   | 5/1994 | Waska et al. |
| 5,324,401 | A | * | 6/1994 | Yeung ............ G01N 27/44721 204/452 |
| 5,636,017 | A |   | 6/1997 | Bruno et al. |
| 6,005,663 | A |   | 12/1999 | Waterhouse et al. |
| 6,191,425 | B1 |   | 2/2001 | Imai |

(Continued)

FOREIGN PATENT DOCUMENTS

| EP | 1932594 A1 | 6/2008 |
|---|---|---|
| WO | 2004017061 A1 | 2/2004 |

OTHER PUBLICATIONS

International Search Report and Written Opinion for International Application No. PCT/US2009/067327, dated Feb. 17, 2010, 16 pages.

(Continued)

*Primary Examiner* — Neil N Turk
(74) *Attorney, Agent, or Firm* — McKee, Voorhees & Sease, PLC (57) ABSTRACT

A multiple capillary florescent detection system employing optical fiber bundles that each fiber bundle has more than one fiber illuminating each sample vessel.

6 Claims, 12 Drawing Sheets

Specification includes a Sequence Listing.

(56) References Cited

U.S. PATENT DOCUMENTS

| | | |
|---|---|---|
| 6,531,044 B1 * | 3/2003 | Anazawa ......... G01N 27/44721 |
| | | 204/452 |
| 6,590,653 B2 | 7/2003 | Parce |
| 6,788,414 B1 | 9/2004 | Yeung et al. |
| 6,838,567 B1 | 1/2005 | Honda et al. |
| 6,944,322 B2 | 9/2005 | Johnson et al. |
| 6,994,348 B2 | 2/2006 | Bradley et al. |
| 7,016,022 B2 | 3/2006 | Fritz et al. |
| 7,029,628 B2 | 4/2006 | Tam et al. |
| 7,084,392 B2 | 8/2006 | DiFoggio et al. |
| 7,379,180 B2 | 5/2008 | Vannuffelen et al. |
| 2002/0097398 A1 | 7/2002 | Parce |
| 2002/0113213 A1 * | 8/2002 | Amirkhanian ... G01N 27/44721 |
| | | 250/458.1 |
| 2003/0116436 A1 * | 6/2003 | Amirkhanian ... G01N 27/44721 |
| | | 204/452 |
| 2005/0030519 A1 | 2/2005 | Roth |
| 2005/0109951 A1 | 5/2005 | Fish et al. |
| 2007/0131870 A1 | 6/2007 | Pang et al. |

OTHER PUBLICATIONS

"Optical Properties of Axial-Illumination Flow Cells for Simultaneous Absorbance-Fluorescence Detection in Micro Liquid Chromatography", Ahmad A. Abbas, Dennis C. Shelly, Department of Chemistry and Biochemistry, Texas Tech University, Lubbock, TX 79409-1061, USA, Journal of Chromatography, Feb. 3, 1995, 17 pages.

* cited by examiner

SEQUENCE LISTING

```
<160> NUMBER OF SEQ ID NOS: 4

<210> SEQ ID NO 1
<211> LENGTH: 161
<212> TYPE: DNA
<213> ORGANISM: Staphylococcus aureus

<400> SEQUENCE: 1
tattctcaat cactggtcgt ggtactgttg ctacaggccg tgttgaacgt ggtcaaatca      60
aagttggtga agaagttgaa atcatcggtt tacatgacac atctaaaaca actgttacag     120
gtgttgaaat gttccgtaaa ttattagact acgctgaagc t                         161

<210> SEQ ID NO 2
<211> LENGTH: 161
<212> TYPE: DNA
<213> ORGANISM: Staphylococcus aureus

<400> SEQUENCE: 2
agcttcagcg tagtctaata atttacggaa catttcaaca cctgtaacag ttgttttaga      60
tgtgtcatgt aaaccgatga tttcaacttc ttcaccaact ttgatttgac cacgttcaac     120
acggcctgta gcaacagtac cacgaccagt gattgagaat a                         161

<210> SEQ ID NO 3
<211> LENGTH: 20
<212> TYPE: DNA
<213> ORGANISM: Artificial Sequence
<220> FEATURE:
<223> OTHER INFORMATION: SYNTHESIZED OLIGO PRIMER

<400> SEQUENCE: 3
tattctcaat cactggtcgt                                                  20

<210> SEQ ID NO 4
<211> LENGTH: 17
<212> TYPE: DNA
<213> ORGANISM: Artificial Sequence
<220> FEATURE:
<223> OTHER INFORMATION: SYNTHESIZED OLIGO PRIMER

<400> SEQUENCE: 4
agcttcagcg tagtcta                                                     17
```

BUNDLED FIBER OPTIC CAPILLARY ELECTROPHORESIS DETECTION SYSTEM

CROSS-REFERENCE TO RELATED APPLICATIONS

This application is a continuation of application Ser. No. 12/634,349 filed Dec. 9, 2009, which claims the benefit of U.S. Provisional Patent Application 61/121,043, filed Dec. 9, 2008, and is also a continuation-in-part of co-pending commonly owned application Ser. No. 11/299,643 filed Dec. 12, 2005.

FIELD OF THE INVENTION

This invention relates to capillary electrophoresis (CE) fluorescence detection systems.

BACKGROUND OF THE INVENTION

Capillary electrophoresis (CE) instruments use electric fields to separate molecules within narrow-bore capillaries (typically 20-100 μm internal diameter). CE techniques are employed in numerous applications, including DNA sequencing, nucleotide quantification, and mutation/polymorphism analysis. Samples analyzed by CE are often detected by fluorescence emission of the sample which has been tagged with a fluorophore. The fluorophores are excited with a light source, and the intensities of the fluorescence emission represent the concentration or amount of the sample components. Generally, the light source is focused on a narrow point on the sample to maximize the energy available for the excitation of fluorophore within the illuminated volume. The detector, which is usually a photomultiplier, photodiode, diode array, or CCD, is positioned to capture the maximum amount of light from the sample, without specific discrimination of the capillary walls or the background.

SUMMARY OF THE INVENTION

Embodiments of the invention provide a high sensitivity and high throughput capillary electrophoresis multi-wavelength florescence detection system. The fluorescent detection system is configured to illuminate a single capillary or a plurality of capillaries, with a pixelated detection system capable of imaging an area of each capillary that differentiates the capillary walls, the space between the capillaries, and the internal liquid volume within the capillary. The detector is coupled to a computer processing system capable of selecting pixels or areas of the image to process (e.g., integrate). The pixels or image area is selected such that only fluorescent light from the internal volume of the capillary, without light from the capillary walls or background light from between the capillaries, is integrated. This results in a larger signal to noise ratio relative to methods that integrate the light from the entire capillary cross-section. The system is configured so that a width of at least one pixel defines the middle liquid volume of each capillary.

Embodiments of the invention also illuminate a relatively large volume of the capillary to maximize the number of fluorophores available for excitation within the illuminated area. This allows for a larger signal to noise ratio relative to methods that integrate light from only a narrowly focused point on the capillary. Further, since embodiments of the invention are able to differentiate between the capillary walls, the space between the capillaries, and the internal liquid volume within the capillary, the computer processing system can process and display the data from the internal liquid volume and exclude the data from the capillary walls and space between the capillaries to provide an excellent signal output even though the large beam area may illuminate capillary walls and space between capillaries.

Some embodiments of the invention include more than one detection window to detect fluorophore emissions at different wavelengths. This allows for detection of multiple compounds within the same column. For example, a series of unknown DNA strands can be labeled with Fluorophore X, while a known standard ladder of DNA strands with known molecular weights can be labeled with Fluorophore Y. The use of multiple detection windows (coupled with multiple light sources), allows for the independent measure of the unknown DNA samples with known standards in a single capillary. This eliminates the need to run a standard compound and unknown compound in two separate capillaries.

BRIEF DESCRIPTION OF THE DRAWINGS

FIG. 6, in the upper portion (A), is an enlarged view of one of the capillaries shown in FIG. 5. FIG. 6, in the lower portion (B), shows a capillary electropherogram trace that represents the summation of all pixels in each column from FIG. 6 (upper portion).

DETAILED DESCRIPTION OF THE PREFERRED EMBODIMENTS

For the purpose of promoting an understanding of the principles of the invention, reference will now be made to the embodiments illustrated in the drawings and specific language will be used to describe the same. It will, nevertheless, be understood that no limitation of the scope of the invention is thereby intended; any alterations and further modifications of the described or illustrated embodiments, and any further applications of the principles of the invention as illustrated therein, are contemplated as would normally occur to one skilled in the art to which the invention relates.

In some embodiments, the invention includes a fluorescence detection system. The detection system includes a sample vessel (e.g., a capillary) in which a sample is placed. A light source is included to emit light to excite a fluorescently labeled sample, and the system is configured to direct light on the sample vessel (sometimes referred to herein as a "detection window") to illuminate a volume of more than about 100 micrometers×$\pi r^2$, where r is one-half of the inner diameter of the sample vessel or capillary. Although the light is intended to illuminate the internal capillary volume, it will also necessarily at least partially illuminate the capillary wall and the space between capillaries. The problem of inadvertent illumination degrades the quality of the output signal, and this problem is exacerbated by the relatively large detection window as described herein.

Embodiments of the invention also include a fluorescence detector capable of imaging the entire cross section of the capillary (or multiple capillaries), and has the resolution to allow it to clearly differentiate between the capillary wall, the internal capillary volume, and the space between capillaries. The detector is positioned to detect the fluorescent emissions of the sample. The detector has the resolution to image distinct parts of the image. For example, the detector can have at least one pixel defining the internal volume of each capillary, at least one pixel defining each capillary wall, and at least one pixel defining the space between the capillaries. Any suitable detector may be used. However, detectors such as charge coupled devices (CCDs) are particularly useful with embodiments of the invention. An example of such a CCD is made by Starlight Xpress Ltd., model#: SXVR-H9, equipped with an ICX285 CCD chip with 1392×1040 pixels in a two-third inch format interline camera and a pixel size of 6.45 μm×6.45 μm.

The detector is attached to a computer system or processor capable of selecting the pixels for the final detection of fluorescent light-whereby only the pixels corresponding to the internal capillary volume are chosen. Pixels corresponding to the capillary walls or the space between capillaries are excluded from the final fluorescent signal. In some embodiments, after the detector (e.g., CCD) records the images, the processor calculates the time lapsed signal to noise ratio of the pixels along the x-axis. The capillary walls always have a lower signal to noise ratio than the illuminated internal volume of the capillary and the space between the capillaries has no signal. Accordingly, the processor (e.g., with software) can use these unique characteristics of each region to define the regions. For example, these data discrimination and analysis functions can be written on Labview version 7.0 form National Instruments run on a personal computer. Accordingly, embodiments of the invention are useful for illuminating a relatively large volume of a fluorescently labeled sample, while excluding stray light from the capillary walls and light from between the capillaries, thereby increasing the signal-to-noise ratio of the illuminated volume to provide a higher quality output.

The fluorescence excitation light source can be a gas discharge lamp (mercury or xenon), a laser (gas, solid state, dye, or semiconductor) or a light-emitting-diode (LED). In some embodiments the detection system includes non-coherent light sources as the excitation light source. In some embodiments, the light source is a high power LED, which operates at a current rating of least 100 milliAmps, preferably at 500 milliAmps, and even more preferably 700 to 1000 milliAmps.

An optical fiber bundle can be provided to direct the emitted light from the light source to the sample vessel detection window without focusing the irradiation light. A large volume of each sample vessel is illuminated due to the non-focused illumination. In some embodiments, the detection window includes a bandpass filter for specific wavelength detection. A fluorescence detector capable of imaging the entire capillary cross-section, with a differentiation of the walls of the capillary, the internal capillary volume, and the space between the capillaries, such as a CCD, is positioned to detect the fluorescent emissions of the sample. In addition, the use of the optical fiber bundle allows the illumination of multiple sample vessels simultaneously in multichannel systems and the detector can monitor fluorescence signals of multiple channels.

Figure 1:
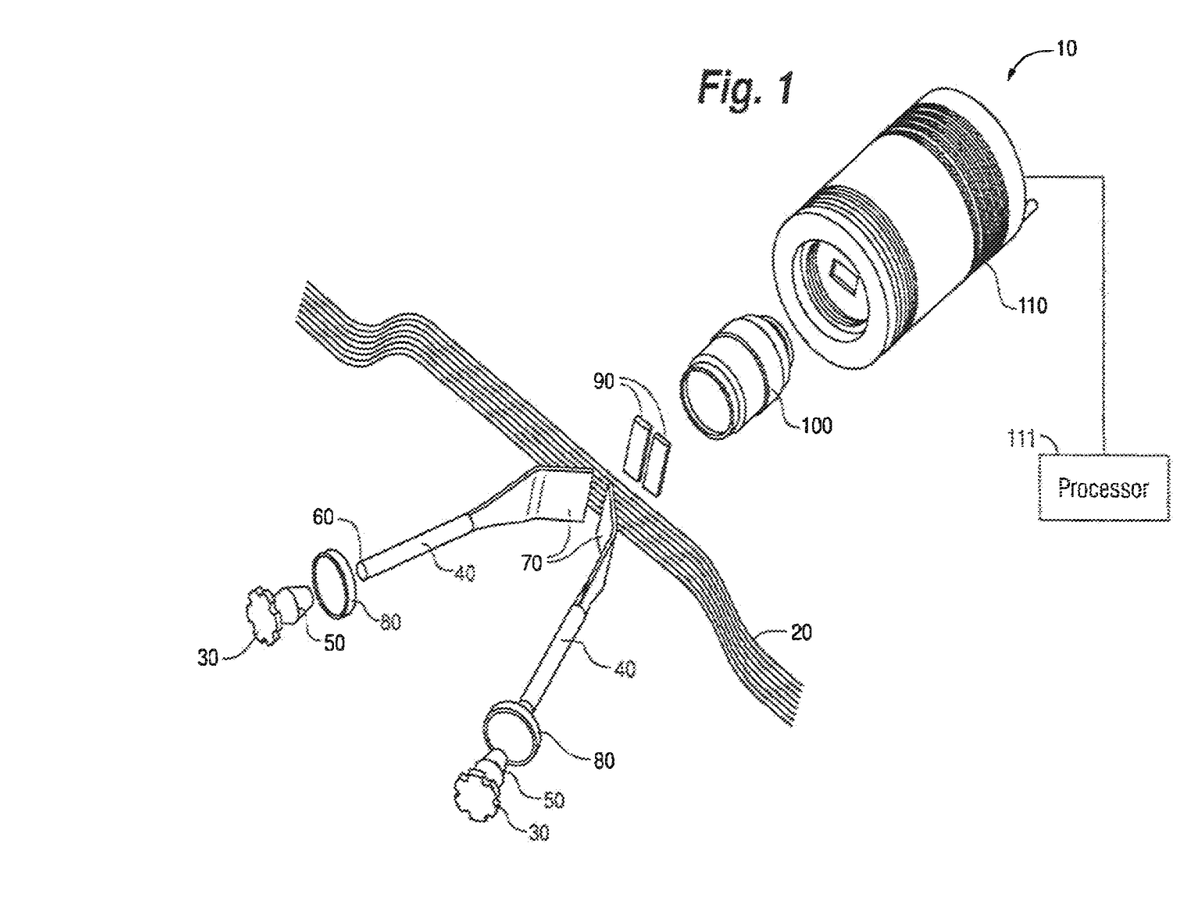
FIG. 1 is a partially exploded schematic diagram illustrating a large volume multiwavelength fluorescence detection system for multiplexed capillary electrophoresis in accordance with an embodiment of the invention.
Figure 2:
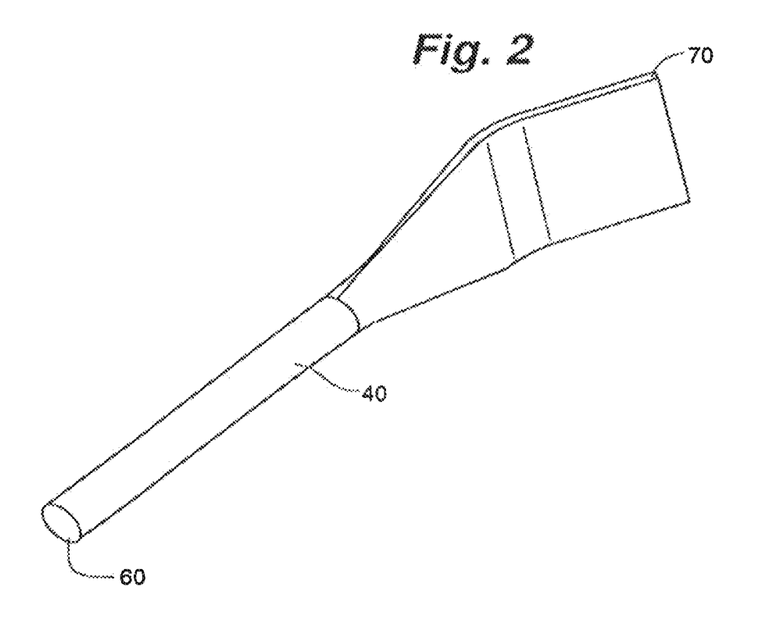
FIG. 2 is a schematic diagram illustrating an optical fiber bundle in accordance with an embodiment of the invention.

FIG. 1 illustrates a fluorescent detection system 10 in accordance with an embodiment of the invention. The embodiment of FIG. 1 includes a multiplexed capillary array electrophoresis system with a capillary array 20 and a high power LED 30 for large volume illumination fluorescence detection. A "high power" LED is one which operates at a current rating of least 100 milliAmps, preferably at 500 milliAmps, and even more preferably 700 to 1000 milliAmps. As shown, the high power LED's light output is coupled to an optical fiber bundle 40 through optical couplers 50. In the embodiment shown, the fiber bundle light entrance end 60 (i.e., proximal end) has a round shape to match the output of the LED while the exit end 70 (i.e., distal end) has a rectangular shape with the long side having similar or larger dimension than the detection window on the multiple capillaries, as shown in FIG. 2. In some embodiments, the optical fiber bundles include about 16,600 optical fibers. Each optical fiber can be about 50 μmin diameter with numeric aperture (N.A.) of about 0.55. The light entrance end can have a diameter of about 7.11 mm to match the optical coupler output area. The exit end of the optical fiber can have dimensions of about 1.5 mm×about 25.4 mm. With this dimension, roughly 30×510 optical fibers are packed into a rectangular shape at the distal end of the optical fiber bundle. In addition, the exit end of the fiber bundle can be positioned at an angle relative to longitudinal axis of the capillary (e.g., between about 30 degrees and 60 degrees, such as about 45 degrees). The angle helps to eliminate the direct irradiation of the excitation light onto the camera lenses to eliminate background noise.

As shown, filters 80 (which can be the same or dissimilar for each other) can be included to block off unwanted excitation wavelengths from the LEDs. Filters 90 (which can be the same or dissimilar for each other) can be used to select the desired fluorescent wavelength for detection. Also as shown, a camera lens 100 can be used to collect the fluorescent emission from the detection windows of the multiple capillaries while a two-dimensional detector such as a CCD 110 can be used to monitor the fluorescent emission. A processor, which would be connected to the CCD to process the output from the CCD (e.g., differentiate the regions and provide an integrated output signal), is not shown.

Embodiments of the invention include configuring the CCD array in such a way as to enable differentiation of the light coming from the capillary walls, the internal capillary volume, and the space between each capillary. This allows one to select and detect light only from the internal volume of each capillary. A CCD with a two-dimensional array area of 1392 by 1040 pixels is preferred for imaging from about 1 up to about 96 capillaries, while enabling differentiation of the walls of the capillary, the internal capillary volume, and the space between the capillaries.

The capillary array electrophoresis system shown in FIG. 1 has capillary windows arranged on the same plane at the detection region to simultaneously illuminate the detection window for on-column detection. During use, the capillary array has both ends immersed into buffer solution in which a high voltage is applied for electrophoresis separation. The ends of the capillary array may be separated for individual sample loading.

Figure 3A:
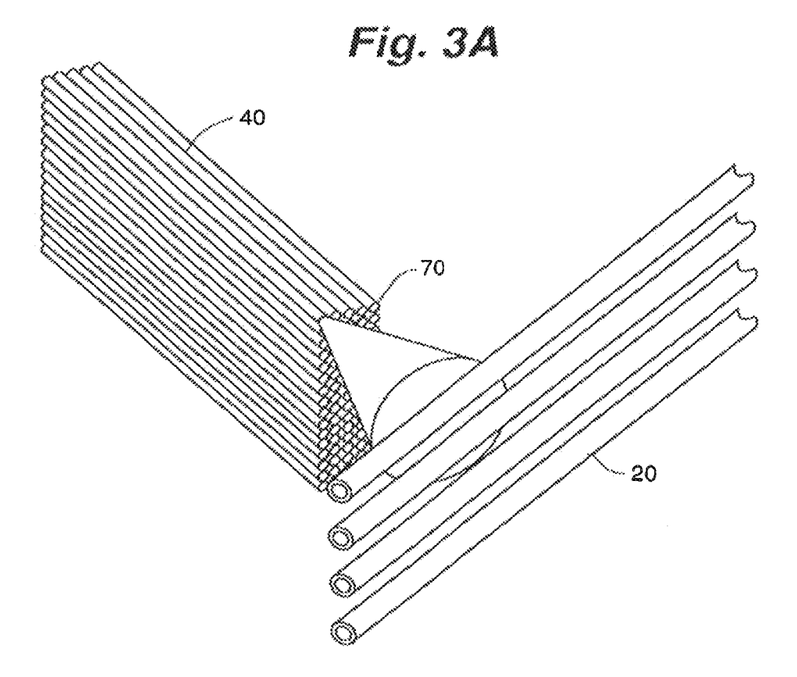
FIG. 3A is a close up view illustrating an optical path in accordance with an embodiment of the invention.
Figure 3B:
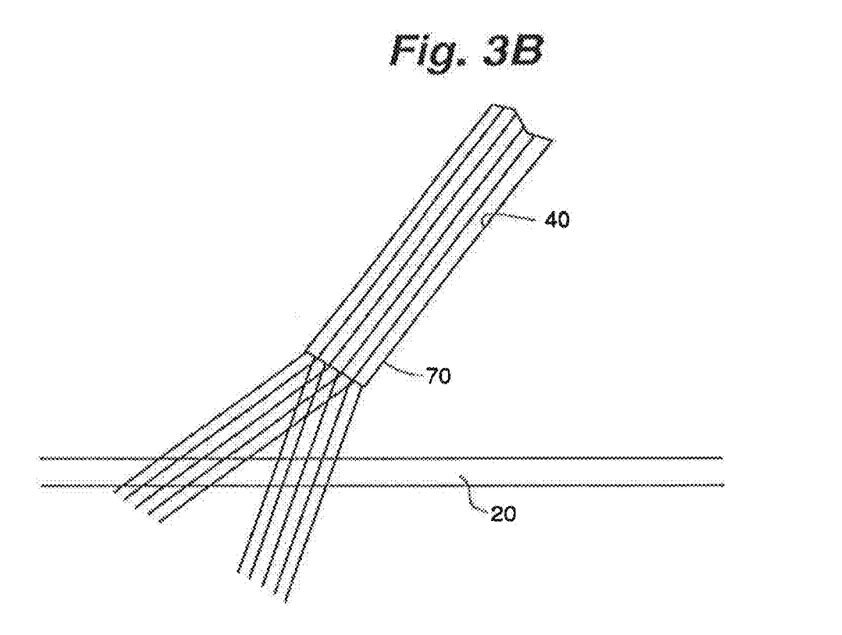
FIG. 3B is a close up view illustrating the optical path in accordance with an embodiment of the invention.

FIGS. 3A and B illustrate close up sections of detection windows in accordance with embodiments of the invention. As shown, the exit end of the optical fiber bundle is positioned less than 1 mm away from the capillaries and at about 45° against the capillaries. The light exits each fiber of the optical fiber bundle with a divergence angle based on the numeric aperture (N.A.) of the optical fiber. For example, an optical fiber has an N.A. of 0.25 will have a divergence angle of about 29° while an N.A. of 0.66 will have divergence angle of about 83°. When the optical fiber bundle is positioned 1 mm or less from the capillary tubing window, approximate 2 mm of the tubing length will be illuminated by the exit light from the optical fiber bundle. In addition, each capillary's detection window will be illuminated by more than one optical fiber from the optical fiber bundle.

Further, in some embodiments, the optical fiber position from the light entrance and exit are randomized. In such embodiments, the uneven light distribution from the LED output is homogenized at the exit end of the optical fiber bundle, which provides more consistent illumination to the sample volume.

Typical fluorescent detection systems focus the light source onto the sample with as small an area as possible. Fluorescent signal intensity is proportional to the incident light power and the amount of fluorophore molecules present in the irradiation volume. Capillaries generally have an internal diameter of about 100 um or less, and fluorescence detection systems for HPLC or capillary electrophoresis system generally focus the light source to a point much less than 100 um. Focusing the light source increases the power density of incident light at the small detection volume. Therefore, more photons are available to excite the sample molecules within the small detection zone (<100 $\mu m \times \pi r^2$, where r is the h of the radius inner tubing of the capillary). Further, focusing the light source into a small area maintains high resolution of separation. If the CE separation resolution is smaller than the illumination area, the detection resolution lost. However, in most of multiplexed capillary electrophoresis applications, the separation resolution does not require the tight focusing (<<100 um).

Therefore, instead of focusing the light to a small volume to obtain high power density for illumination, embodiments of the invention use a high power LED to provide high photon flux to illuminate a relatively large volume in which more molecules are excited to fluorescence because more sample molecules are available for excitation. In some embodiments, the system is configured to direct light on the sample vessel to illuminate a volume of more than about 50 micrometers×$\pi r^2$ where r is one-half of the inner diameter of the sample vessel. In other embodiments, the system is configured to direct light on the sample vessel to illuminate a volume of more than about 500 micrometers×$\pi r^2$. In yet other embodiments, the system is configured to direct light on the sample vessel to illuminate a volume of more than about 1,000 micrometers×$\pi r^2$. In certain embodiments, the system is configured to direct light on the sample vessel to illuminate a volume of more than about 1,500 micrometers× $\pi r^2$. In some embodiments, the system is configured to direct light on the sample vessel to illuminate a volume of less than about 2,000 micrometers×$\pi r^2$. In certain embodiments, the system is configured to direct light on the sample vessel to illuminate a volume of about 2,000 micrometers×$\pi r^2$.

Figure 4:
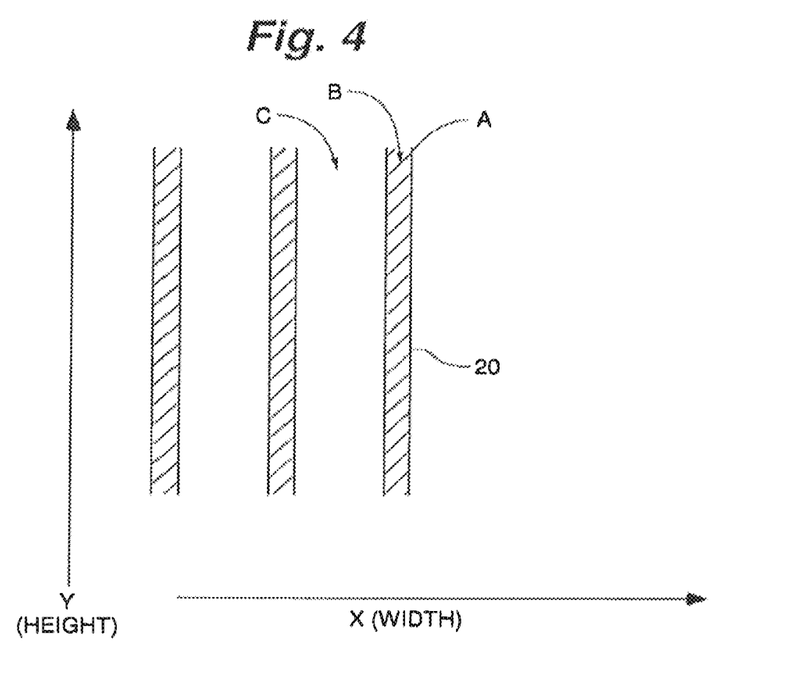
FIG. 4 is a schematic of a CCD array image showing a differentiation of internal capillary volume, liquid capillary walls, and space between the capillaries.

As shown in FIG. 4, the CCD detector should be configured to detect three regions of the capillary (for a single capillary) or capillary array (for multiple capillaries). In FIG. 4, region A includes the wall of each capillary, region B includes the internal volume of each capillary, and region C includes the space between capillaries. Each region should correspond to at least one distinct pixel in the detector. In some embodiments, region B (of each capillary) has at least 3 pixels. In other embodiments, region B (of each capillary) has at least 5 pixels.

Figure 5:
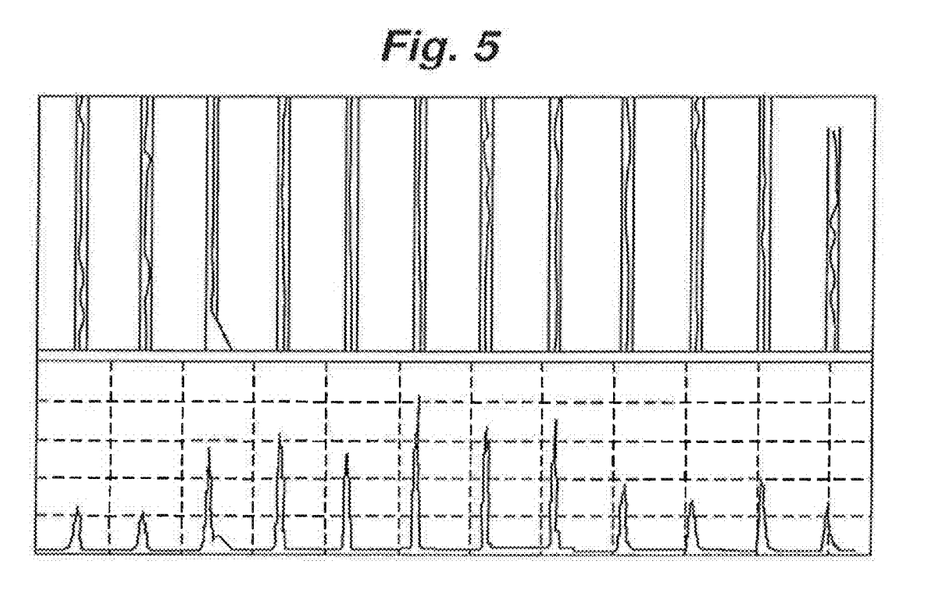
FIG. 5 is a picture of an imaged capillary array, showing a clear differentiation of internal capillary liquid, capillary walls, and space between the capillaries.
Figure 6:
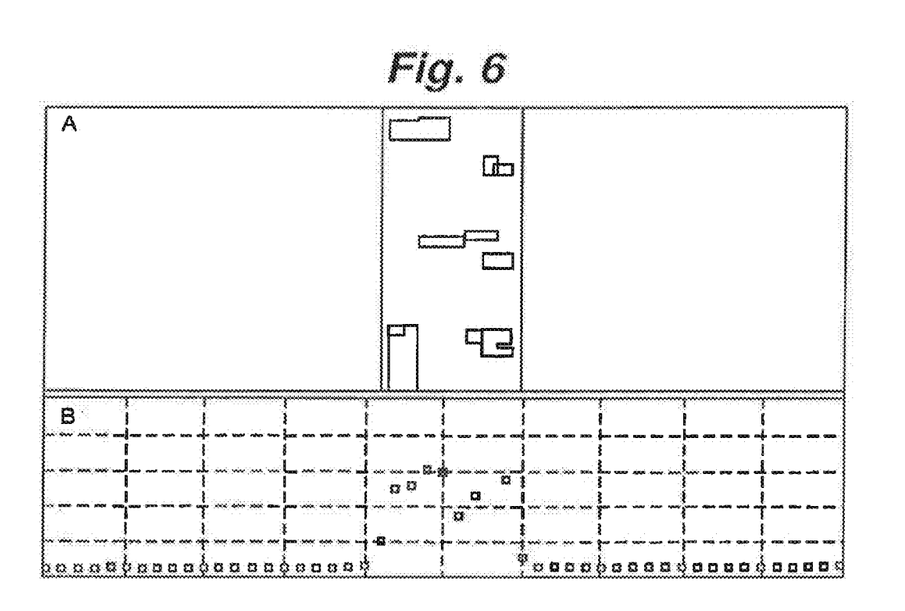

The height of the entire capillary array image may range from 1 pixel up to the y-axis length (in pixels) of the CCD. For example, A CCD array with width of 1392 pixels and length (y-axis) of 1040 pixels may be used to image a 12-capillary system wherein the internal liquid volume width (x-axis) of each capillary is at least 6 pixels, the walls of each capillary (x-axis) is at least I-pixel, and the space between each capillary is at least 20 pixels. The height of each image is at least 60 pixels, but may be up to 1040 pixels, depending on how the capillary image is focused onto the CCD window. FIG. 5 shows an imaged capillary array, in which the internal volume of each capillary is about 6 pixels, each capillary wall is 2 pixels, and the space between capillaries is about 80 pixels. The length of the capillary image is about 60 pixels. A CCD detector with 1392 by 1040 pixels was used to capture this image. FIG. 6 shows an enlarged view of one of the capillaries from FIG. 5. The two vertical lines represent the wall of the capillary. The uneven light distribution from the capillary is due to scattering from imperfect surface, dust, and incomplete removal of polyimide coating. FIG. 6 (lower portion) shows the one dimensional display when summing all vertical pixels intensities together for each column.

Figure 7:
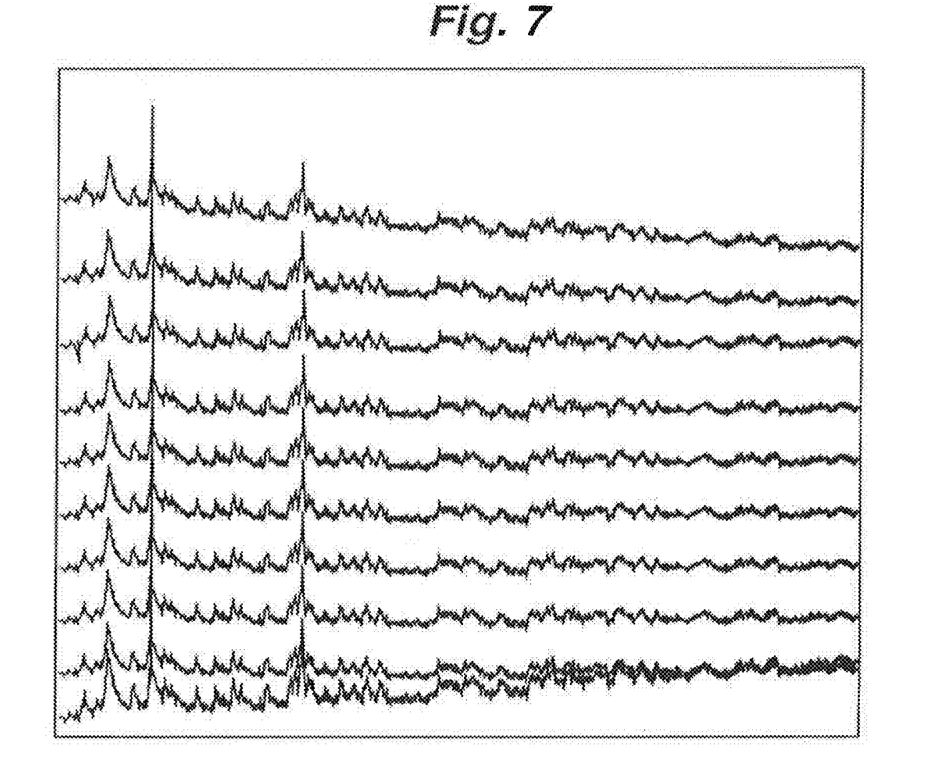
FIG. 7 is a series of electropherograms of single stranded DNA that represents the summation of all pixels in each column from edge to edge of the capillary shown in FIG. 6.
Figure 8:
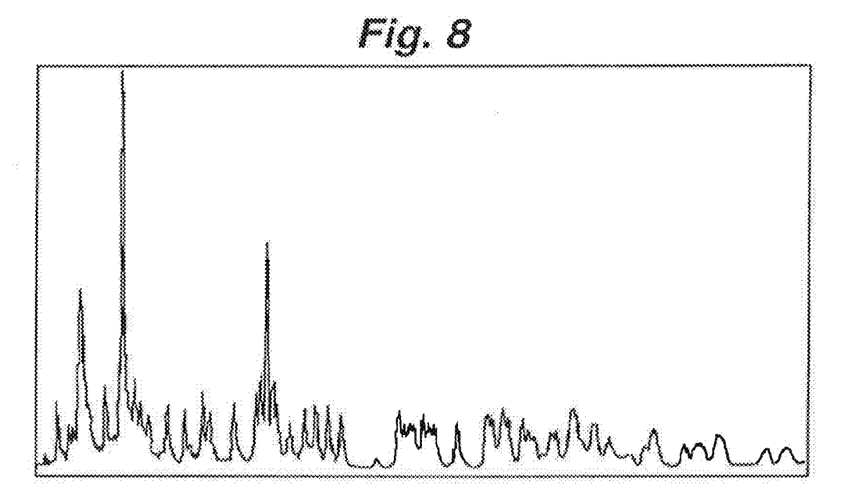
FIG. 8 is an electropherogram constructed from the middle 6 electropherograms from FIG. 7 (i.e. excluding light from the walls of the capillary).

FIG. 7 shows the electropherograms of single stranded DNA separation. A sample similar to that illustrated in example 3 was used here for demonstration. Only one LED and fiber optical bundle was used for the excitation. A LED with 470 nm emission was used for the excitation while monitoring the fluorescence signal through a band pass filter with bandwidth from 500 nm to 550 nm. The samples were injected into one end of the capillaries by applying 5 kV for 20 seconds. After the sample injection, the injection ends of the capillaries were immersed into buffers for separation under 150 V/cm separation field strength. The fluorescent signal was recorded by a CCD capable of imaging the entire cross-section of the capillary, including the capillary walls, the volume within each capillary, and the space between each capillary. Each electropherogram represents the time lapse signal from the summation of all vertical pixels signal of each column (vertical line to vertical line) shown in FIG. 6 (upper portion). The top trace to the bottom trace in FIG. 7 shows 10 electropherograms that represent each column's (i.e. a column with a width of 1 pixel) signal during the time of electrophoresis separation. The top trace is the left edge of the capillary, and the bottom trace is the right edge of the capillary. FIG. 7 indicates that the capillary image had two pixels for each side of wall with significantly lower S/N and 6 pixels for the internal volume with high S/N. An average of all 10 electropherograms, including the wall, results in a lower signal to noise ratio than an average of the middle 8 electropherograms. To obtain a higher signal to noise ratio the wall's signal should be excluded and only the internal volume signal used to construct the final electropherogram. FIG. 8 shows the final electropherogram excluding the signal from the capillary's wall.

Figure 9:
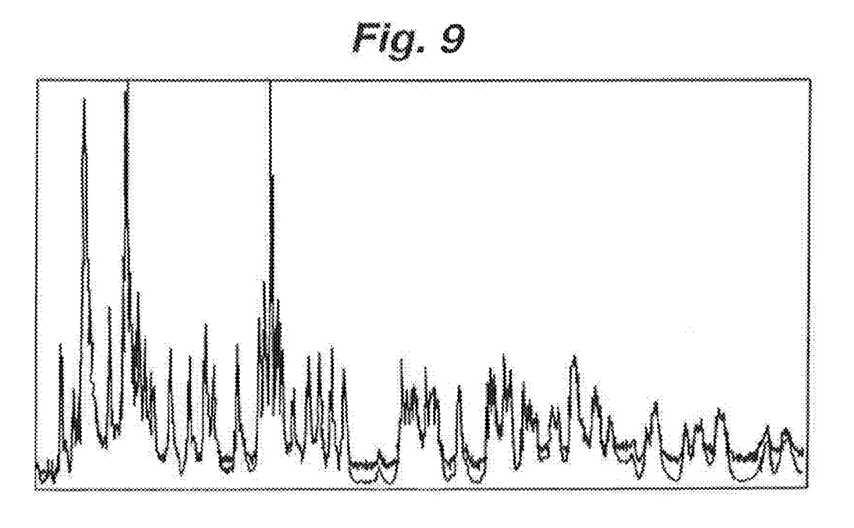
FIG. 9 is an electropherogram measured with large volume fluorescence detection as discussed in FIG. 8 (lower trace) compared with an electropherogram using a small volume fluorescence detection (top trace).

With the same irradiance, large volume fluorescence detection provides better S/N compared to small volume fluorescence detection since more sample molecules are available for detection. In FIG. 9, the bottom electropherogram was constructed using large volume fluorescence detection, in which a 1.5 mm section of capillary was illuminated; while the top electropherogram represented the small volume fluorescence detection, in which only a 50 µm section of capillary was illuminated. The electropherogram has much better SIN for large volume fluorescence detection (lower trace) than the small volume fluorescence detection (top trace).

In addition, as shown in FIG. 1, embodiments of the invention provide for multiwavelength excitation and fluorescent detection. If the sample has been labeled with two different fluorophores, it may require two different wavelengths for excitation because of the absorption coefficiency is different for different fluorophores. Embodiments of the invention provide for multiple wavelength excitation and detection with the use of LEDs at different wavelengths to irradiate at different locations for different wavelength excitation and detection.

In such embodiments, as shown in FIG. 1, multiple light sources and optical fiber bundles are used for excitation at multiple detection windows to excite the fluorophore at multiple wavelengths. In some embodiments, each detection window comprises a bandpass filter for specific wavelength detection. All detection windows can be monitored simultaneously with a two-dimensional detector such as a charged coupled device (CCD) capable of imaging the entire cross-section of the capillaries, with a clear pixelated differentiation of the capillary walls, the internal capillary volume, and the space between the capillaries, as described in detail above. When coupled with a computer system capable of selecting individual pixels for integration, such that pixels corresponding to the walls of the capillary are excluded from integration, this allows for an increase in the signal-to-noise ratio. When multiple detection windows are used, multiwavelength fluorescence signals from the same separation sample vessel are obtained. In addition, the use of optical fiber bundle allows the illumination of multiple sample vessels simultaneously in multi-channel systems and the two-dimensional detector can monitor multiwavelength fluorescence signals of multiple channels.

EXAMPLES

The examples below are merely illustrative and are not intended to limit the scope of the invention.

Example 1

Double Stranded DNA Electropherogram and a Large Volume Detection System

Figure 10:
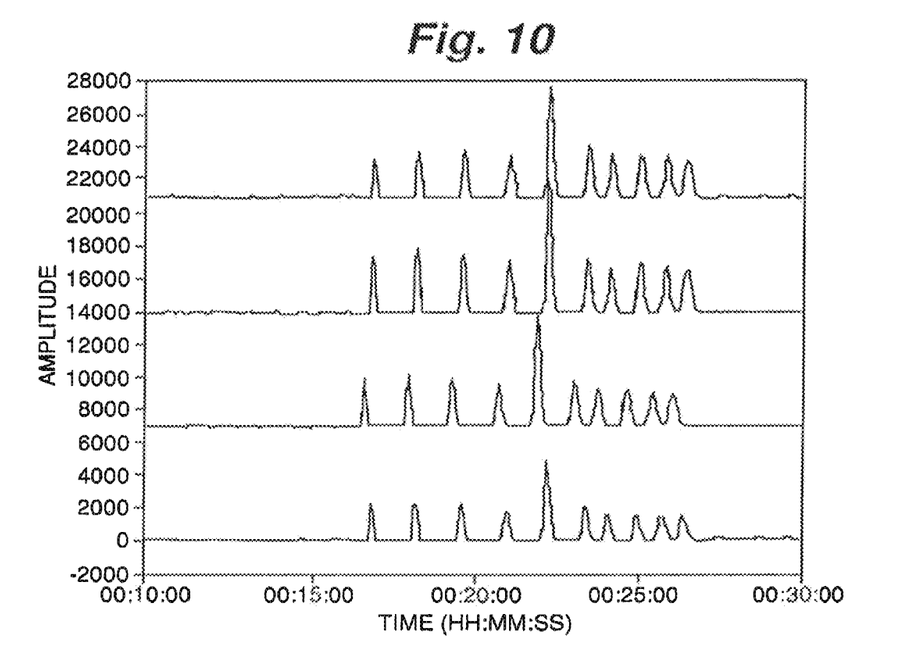
FIG. 10 is a double stranded DNA electropherogram with single wavelength large volume fluorescence detection as discussed in Example 1, wherein each separate electropherogram is from a separate capillary.

FIG. 10 shows the electrophoretic pattern of double-stranded DNA 100 b.p. ladders obtained by an embodiment of the invention. This was measured in a multicapillary system, and each trace represents a different capillary. In this example only one LED light source and fiber optical bundle was used for the fluorophore excitation. The LED emitted at 470 nm for excitation while a band pass filter transmitted from 500 nm to 600 nm was used to select the desire fluorescent wavelength for detection. The separation matrix contained SYBR Green dye. When double-stranded DNA binds to SYBR Green, the resulting DNA dye complex absorbs the LED light and fluoresces at 522 nm. The samples were injected into one end of the capillaries by applying 5 kV for 5 seconds. After the sample injection, the injection ends of the capillaries were immersed into buffers for separation under 150 V/cm of a constant electric field. The volume of illuminated liquid was
1500 micrometers×$\pi r^2$, where r is one-half of the inner diam-eter of the sample vessel, which was 75 um.

Example 2

Figure 11:
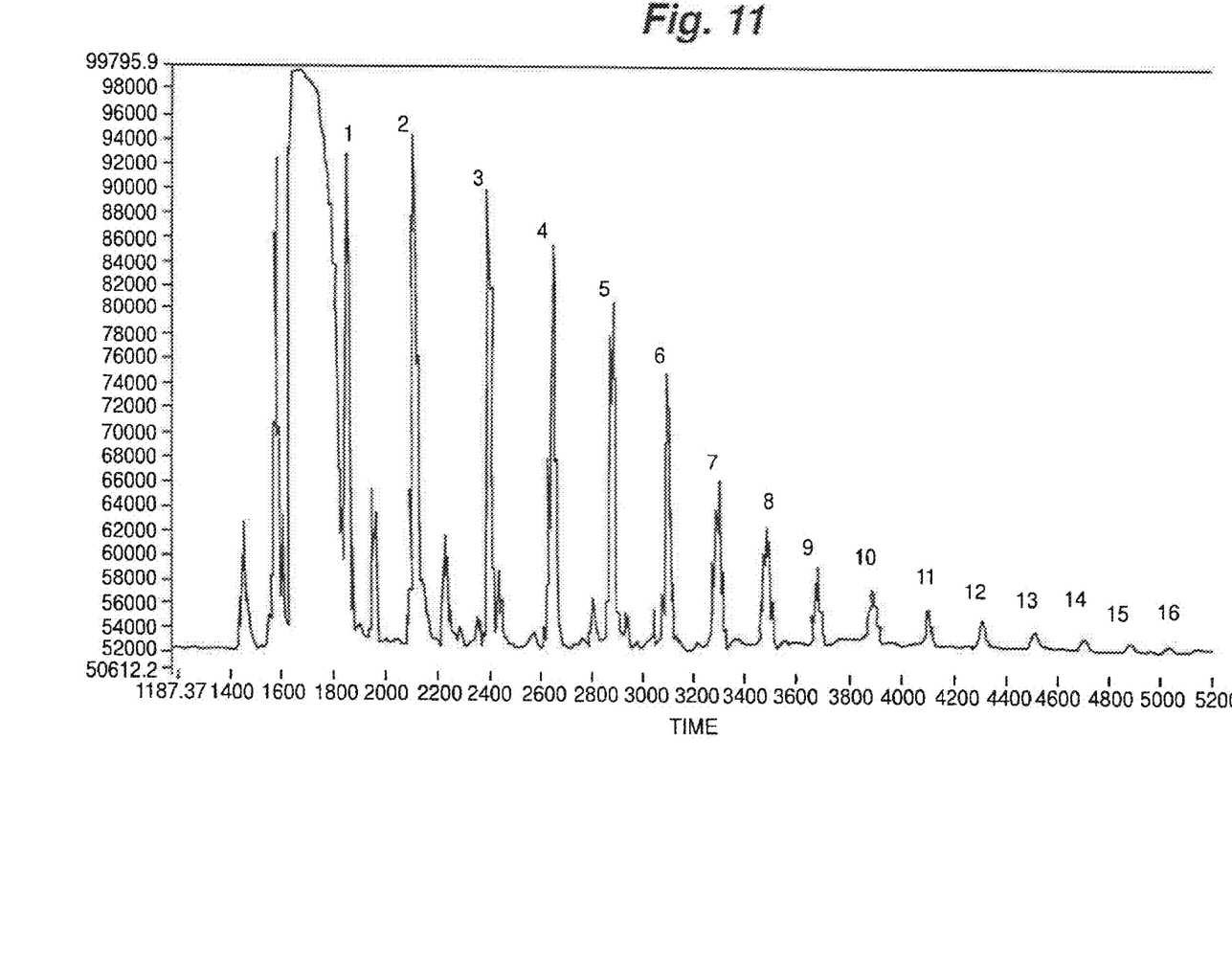
FIG. 11 is a carbohydrate (MALTRIN® M-200) separation electropherogram with single wavelength large volume fluorescence detection as discussed in Example 2.

Carbohydrate Separation Electropherogram with Large Volume Fluorescence Detection FIG. 11 shows the high resolution oligosaccharide profiling by electrophoretic separation of carbohydrate MALTRIN® M-200 labeled with 8-aminopyrene-1,3,6-trisulfonate (APTS) using an embodiment of the invention. In this example only one LED and fiber optical bundle was used for the excitation. A LED with 470 nm emission was used for the excitation while monitoring the fluorescence signal through a band pass filter with bandwidth from 500 nm to 600 nm. The volume of liquid illuminated was 1500 micrometers×$\pi r^2$, where r is one-half of the inner diameter of the sample vessel, which was 75 um. The samples were injected into one end of the capillaries by applying 5 kV for 10 seconds. After the sample injection, the injection ends of the capillaries were immersed into buffers for separation under 300 V/cm of a constant electric field. The fluorescent signal was recorded by the CCD. MALTRIN® M-200 is a maltooligosaccharide ladder which contains at least 16 individual oligomers as shown in FIG. 11.

Example 3

Multiple Wavelength Detection

The *Staphylococcus aureus* tuf gene has the following DNA sequence:

5'-<u>TATTCTCAATCACTGGTCGT</u>GGTACTGTTGCTACAGGCCGTGTTGAA
3'-<u>ATAAGAGTTAGTGACCAGCA</u>CCATGACAACGATGTCCGGCACAACTT

CGTGGTCAAATCAAAGTTGGTGAAGAAGTTGAAATCATCGGTTTACATGA
GCACCAGTTTAGTTTCAACCACTTCTTCAACTTTAGTAGCCAAATGTACT

CACATCTAAAACAACTGTTACAGGTGTTGAAATGTTCCGTAAATTAT<u>TAG</u>
GTGTAGATTTTGTTGACAATGTCCACAACTTTACAAGGCATTTAATA<u>ATC</u>

<u>ACTACGCTGAAGCT</u>-3' (SEQ ID NO: 1)
<u>TGATGCGACTTCGA</u>-5' (SEQ ID NO: 2)

The following DNA sequences were selected as primers for PCR amplification:

(SEQ ID NO: 3)
5'-TATTCTCAATCACTGGTCGT-3'

(SEQ ID NO: 4)
5'-AGCTTCAGCGTAGTCTA-3'.

5'-TATTCTCAATCACTGGTCGT-3' (SEQ ID NO:3) was labeled with a fluorescence dye (FAM) in the 5' position, and 5'-AGCT-TCAGCGTAGTCTA-3' (SEQ ID NO: 4) was labeled with a different fluorescence dye (Cy-5) at the 5' position. After the PCR amplification for *Staphylococcus aureus* DNA, one strand of PCR product contained a green fluorescence dye while other strand of DNA contained a red fluorescence dye. After purification of the PCR product, 80% of N-methylformamide was used to cleave the DNA at 110° C. for 30 minutes. Samples were then separated with electrophoresis without further purification.

Figure 12:
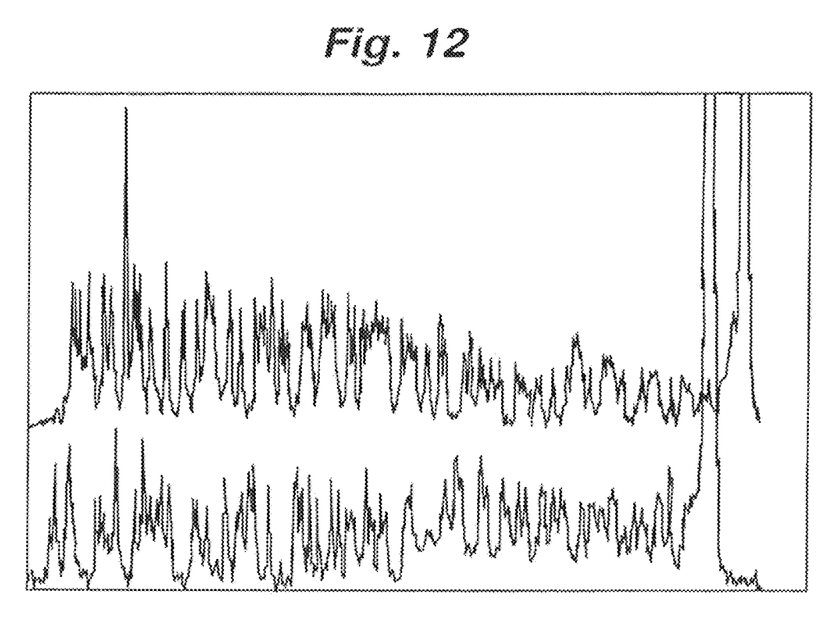
FIG. 12 is two electropherograms (one for each wavelength) generated with a two wavelength large volume fluorescence detection as discussed in Example 3.

A capillary fluorescent detection system in accordance with the invention was used to simultaneously separate and detect the fragments that labeled with the different dyes. The embodiment of the invention shown in FIG. 1 was used for the separation and detection. FIG. 12 shows the electropherograms obtained with the present two wavelength (i.e., colors) detection system. The bottom trace represents the emission wavelength from 500 nm to 550 nm with excitation at 470 nm while the top trace represents the emission wave-length from 620 nm and up with the excitation at 560 nm. The volume of illuminated liquid was 1500 micrometers×$\pi r^2$, where r is one-half of the inner diameter of the sample vessel, which was 75 um. The 480 nm to 550 nm represents the emission from FAM labeled DNA fragments while the other wavelength represents the emission from Cy-5 labeled DNA fragments.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations, which fall within the spirit and broad scope of the invention.

What is claimed is:

1. A multiplex capillary fluorescent detection system, comprising:
   a plurality of capillaries having an internal radius;
   a high power LED light source for providing a high photon flux to illuminate a volume selected from the group consisting of more than about 500 micrometers$*\pi*r^2$, more than about 1000 micrometers$*\pi*r^2$, more than about 1500 micrometers$*\pi*r^2$, and more than about 2000 micrometers$*Pi*\pi^2$, wherein r is the internal radius of the capillaries;
   said high power LED light source being optically coupled to an optical fiber bundle that transmits light emitted from the high power LED light source to said plurality of capillaries;
   said optical fiber bundle containing at least two individual optical fibers;
   and wherein the ends of said at least two individual fibers in said optical fiber bundle are adjacent to each other and lie on a single plane;
   at least one of said individual fibers in said optical fiber bundle provides for illuminating a whole volume of at least two of said capillaries;
   and a CCD detector positioned to receive and detect fluorescence emissions from the capillaries.

2. The multiplex capillary fluorescent detection system of claim 1, wherein the distal end of said optical fiber bundle includes a generally rectangular shape.

3. The multiplex capillary florescent detection system of claim 2, wherein light transmitted through said fiber optic bindle with said generally rectangular shape illuminates all sample vessels simultaneously.

4. The fluorescence detection system of claim 1, wherein the detection system includes at least two light sources.

5. A method of detecting a fluorescence emission in a fluorescently labeled sample, the method comprising:
   introducing said fluorescently labeled sample into a plurality of capillaries having an internal radius;
   providing a high photon flux of transmitted light from a high power LED to illuminate a volume selected from the group consisting of more than about 500 micrometers$*\pi*r^2$, more than about 1000 micrometers$*\pi*r^2$, more than about 1500 micrometers$*\pi*r^2$, or more than about 2000 micrometers$*\pi*r^2$ into and through a fiber optic bundle containing at least two individual fibers, wherein r is the internal radius of the capillaries,
   wherein the ends of said at least two individual optical fibers in said optical fiber bundle are adjacent to each other and lie on a single plane;
   at least one of said individual fibers in said optical fiber bundle illuminates a whole volume of at least two of said capillaries;
   wherein said transmitted light through said optic fiber bundle illuminates all of said plurality of capillaries simultaneously;
   and detecting fluorescent emissions from said capillaries by a CCD detector.

6. The system of claim 1 wherein the optical fiber bundle has an exit end, and the capillaries are positioned less than one millimeter away from said end; wherein said optical fiber bundle is not immediately adjacent to said capillaries.

* * * * *

UNITED STATES PATENT AND TRADEMARK OFFICE
CERTIFICATE OF CORRECTION

PATENT NO. : 10,408,790 B2  
APPLICATION NO. : 15/001632  
DATED : September 10, 2019  
INVENTOR(S) : Ho-ming Pang et al.

Page 1 of 1

It is certified that error appears in the above-identified patent and that said Letters Patent is hereby corrected as shown below:

On the Title Page

In item (57), in Column 2, in "Abstract", Line 1, delete "florescent" and insert -- fluorescent --, therefor.

In the Specification

In Column 5, Line 64, delete "πr²" and insert -- $\pi r^2$, --, therefor.

In Column 7, Line 18, delete "SIN" and insert -- S/N --, therefor.

In Column 7, Line 25, delete "coefficiency" and insert -- coefficient --, therefor.

In Column 8, Lines 13-14, delete "1500 micrometers×πr², where r is one-half of the inner diam-eter of the sample vessel, which was 75 um." and insert the same on Column 8, Line 12, as a continuation of the same paragraph.

In Column 8, Line 14, delete "diam-eter" and insert -- diameter --, therefor.

In the Claims

In Column 11, Line 19, in Claim 1, after "individual" insert -- optical --.

In Column 11, Line 30, in Claim 3, delete "florescent" and insert -- fluorescent --, therefor.

In Column 11, Line 32, in Claim 3, delete "bindle" and insert -- bundle --, therefor.

In Column 12, Line 30, in Claim 6, after "said" insert -- exit --.

Signed and Sealed this  
Second Day of June, 2020

Andrei Iancu  
*Director of the United States Patent and Trademark Office*